United States Patent
Siddique et al.

(12)

(10) Patent No.: US 6,268,170 B1
(45) Date of Patent: *Jul. 31, 2001

(54) α-TOCOPHEROL TRANSPORT PROTEIN: COMPOSITIONS AND METHODS

(75) Inventors: Teepu Siddique, Evanston; Afif Hentati; Han-Xiang Deng, both of Chicago, all of IL (US)

(73) Assignee: Northwestern University, Evanston, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/557,614

(22) Filed: Nov. 14, 1995

(51) Int. Cl.[7] .................... C07K 14/705; C12N 15/10; C12N 5/10
(52) U.S. Cl. .................... 435/69.1; 530/350; 536/23.1; 536/23.5; 536/24.1; 435/320.1; 435/325; 435/252.3; 435/254.11; 514/12; 549/408
(58) Field of Search .................... 530/350, 388.85; 549/408; 435/69.1, 320.1, 240.2, 243, 252.8, 6, 325, 252.3, 254.11; 436/501; 536/23.5, 23.1, 24.1; 514/12

(56) References Cited

U.S. PATENT DOCUMENTS 5,541,220 * 7/1996 Ismail et al. .................... 514/458

OTHER PUBLICATIONS

Arita et al., Human alpha–tocopherol transfer protein: cDNA cloning, expression and chromosomal localization, Biochem. J., 306(pt. 2): 437–443, Mar. 1995.*

Ouahchi et al., Ataxia with isolated vitamin E deficiency is caused by mutations in the alpha–tocopherol transfer protein, Nat. Genetics, 9: 141–145, Feb. 1995.*

Langer, R., New methods of drug delivery, Science, 249: 1527–1532, Sep. 1990.*

* cited by examiner

*Primary Examiner*—Lorraine Spector
*Assistant Examiner*—Claire M. Kaufman
(74) *Attorney, Agent, or Firm*—Rockey, Milnamow & Katz

(57) ABSTRACT

The present invention provides an isolated and purified α-tocopherol transport protein polypeptide. Human recombinant α-tocopherol transport protein, polynucleotides encoding human α-tocopherol transport protein and methods of using α-tocopherol transport protein polypeptides and polynucleotides are also provided.

13 Claims, 2 Drawing Sheets

FIG. 1

GGCGGGCATGGCAGAGGCGCGATCCCAGCCCTCGGCGGGGCCGCAGCTCAAC
GCGCTACCGGACCACTCTCCGTTGCTGCAGCCGGGCCTGGCGGCGCTGCGGC
GCCGGGCCCGGGAAGCTGGCGTCCCGCTCGCGCCGCTGCCGCTCACCGACTC
CTTCCTGCTGCGGTTCCTGCGCGCCCGGGATTTCGATCTGGACCTGGCCTGG
CGGTTACTAAAAACTATTATAAGTGGAGAGCAGAATGTCCAGAAATAAGTG
CAGATCTACACCCTAGAAGTATTATTGGCCTCCTAAAGGCTGGCTACCATGG
AGTCCTGAGATCCAGGGATCCACTGGCAGCAAAGTTCTTATTTACAGAATC
GCACACTGGGACCCCAAAGTTTTTACAGCTTATGACGTATTTCGAGTAAGTC
TAATCACATCCGAGCTTATTGTACAGGAGGTAGAAACTCAGCGGAATGGAAT
CAAGGCTATCTTTGATCTGGAAGGTTGGCAGTTTTCTCATGCTTTTCAAATC
ACTCCATCCGTAGCCAAGAAGATTGCTGCTGTACTTACGGATTCATTTCCAT
TGAAAGTTCGTGGCATCCATTTGATAAATGAACCAGTAATTTTCCATGCTGT
CTTTTCCATGATCAAACCATTCCTGACTGAAAAATTAAGGAACGGATTCAC
ATGCATGGGAACAACTACAAACAAAGCTTGCTTCAGCATTTCCCAGACATTC
TTCCTCTGGAATATGGTGGTGAAGAATTCTCCATGGAGGACATTTGTCAGGA
ATGGACAAATTTTATAATGAAGTCTGAAGATTATCTCAGGAGCATTTCTGAG
AGCATTCAATGAGAAGTTATGTCATGTGAATGGCTTCCTAACTAAAATCATG
GTGATATCCAACTGGTTAATTGATTGAAGA-3' (SEQ ID NO:1)

CCGCCCGTACCGTCTCCGCGCTAGGGTCGGGAGCCGCCCCGGCGTCGAGTTG
CGCGATGGCCTGGTGAGAGGCAACGACGTCGGCCCGGACCGCCGCGACGCC
GCGGCCCGGGCCCTTCGACCGCAGGGCGAGCGCGGCGACGGCGAGTGGCTG
AGGAAGGACGACGCCAAGGACGCGCGGGCCCTAAAGCTAGACCTGGACCGG
ACCGCCAATGATTTTTTGATAATATTCACCTCTCGTCTTACAGGTCTTTATTCA
CGTCTAGATGTGGGATCTTCATAATAACCGGAGGATTTCCGACCGATGGTACC
TCAGGACTCTAGGTCCCTAGGGTGACCGTCGTTTCAAGAATAAATGTCTTAGC
GTGTGACCCTGGGGTTTCAAAAATGTCGAATACTGCATAAAGCTCATTCAGAT
TAGTGTAGGCTCGAATAACATGTCCTCCATCTTTGAGTCGCCTTACCTTAGTTC
CGATAGAAACTAGACCTTCCAACCGTCAAAGAGTACGAAAGTTTAGTGAG
GTAGGCATCGGTTCTTCTAACGACGACATGAATGCCTAAGTAAAGGTAACTTT
CAAGCACCGTAGGTAAACTATTTACTTGGTCATTAAAAGGTACGACAGAAAA
GGTACTAGTTTGGTAAGGACTGACTTTTTTAATTCCTTGCCTAAGTGTACGTA
CCCTTGTTGATGTTTGTTTCGAACGAAGTCGTAAAGGGTCTGTAAGAAGGAG
ACCTTATACCACCACTTCTTAAGAGGTACCTCCTGTAAACAGTCCTTACCTGTT
TAAAATATTACTTCAGACTTCTAATAGAGTCCTCGTAAAGACTCTCGTAAGTT
ACTCTTCAATACAGTACACTTACCGAAGGATTGATTTTAGTACTCACTATAGG
TTGACCAATTAACTAACTTCT-3' (SEQ ID NO:3)

FIG. 2

```
HUMAN    1  MAEARSQPSAGPQLNALPDHSPLLQPGLAALRRRAREAGVPLAPLPLTDSFLLRFLRARD   60
            ||| | |   ||| ||| ||||||  ||||||  ||||||  ||| |  ||||||||||
RAT      1  MAEMRPGPVVGKQLNEQPDHSPLVQPGLAELRRRAQEEGVPETPQPLTDAFLLRFLRARD   60

HUMAN   61  FDLDLAWRLLKNYYKWRAECPEISADLHPRSIIGLLKAGYHGVLRSRDPTGSKVLIYRIA  120
            ||||||||||||||||||||||||||||||||| |||||||||||||||||| |||||
RAT     61  FDLDLAWRLMKNYYKWRAECPELSADLHPRSILGLLKAGYHGVLRSRDPTGSRVLIYRIS  120

HUMAN  121  HWDPKVFTAYDVFRVSLITSELIVQEVETQRNGIKAIFDLEGWQFSHAFQITPSVAKKIA  180
             |||||||||||||||||||||||||||||| ||||||||||| ||||||||||||||
RAT    121  YWDPKVFTAYDVFRVSLITSELIVQEVETQRNGVKAIFDLEGWQISHAFQITPSVAKKIA  180

HUMAN  181  AVLTDSFPLKVRGIHLINEPVIFHAVFSMIKPFLTEKIKERIHMHGNNYKQSLLQHFPDI  240
            || ||||||||||||||||||||||||||||||||||||| | |||||||| ||||||
RAT    181  AVVTDSFPLKVRGIHLINEPVIFHAVFSMIKPFLTEKIKGRIHLHGNNYKSSLLQHFPDI  240

HUMAN  241  LPLEYGGEEFSMEDICQEWTNFIMKSEDYLRSISESIQ  278  SEQ ID NO:2
            ||||||| | |||||||||||||||||||| |||| ||
RAT    241  LPLEYGGNESSMEDICQEWTNFIMKSEDYLSSISETIQ  278  SEQ ID NO:23
```

α-TOCOPHEROL TRANSPORT PROTEIN: COMPOSITIONS AND METHODS

DESCRIPTION

1. Technical Field of the Invention

The field of this invention is α-tocopherol transport protein. More particularly, the present invention pertains to human α-tocopherol transport protein, polynucleotides encoding that α-tocopherol transport protein, and methods of making and using those polynucleotides and proteins.

2. Background of the Invention

Familial isolated vitamin E deficiency, also called ataxia with vitamin E deficiency (AVED) is a neurodegenerative syndrome characterized by cerebellar ataxia and symptoms of central and peripheral axonopathy resembling Friedreich ataxia. It is transmitted as an autosomal recessive trait. The failure to incorporate α-tocopherol in very low density lipoprotein (VLDL) in liver cells is thought to be the primary cause of the decrease in the serum level of vitamin E in these patients. The absorption and metabolism of chylomicrons and VLDL are normal in AVED patients. This differentiates AVED from most causes of secondary vitamin E deficiency in which the perturbation of lipoprotein absorption, metabolism or transport is the primary cause of vitamin E deficiency. α Tocopherol transfer protein (αTTP) from rat liver enhances the transfer of the α-tocopherol form of vitamin E between membranes. In vivo, αTTP incorporates α-tocopherol into lipoprotein particles during their assembly in the liver cells. A recent report has identified three mutations in two exons of the gene for αTTP in families with AVED.

BRIEF SUMMARY OF THE INVENTION

In one aspect, the present invention provides an isolated and purified polynucleotide comprising a nucleotide sequence consisting essentially of a nucleotide sequence selected from the group consisting of (a) nucleotide position 8 to nucleotide position 842 of the sequence of SEQ ID NO:1; (b) sequences that are complementary to the sequences of (a), and (c) sequences that, when expressed, encode a polypeptide encoded by a sequence of (a). A preferred polynucleotide is a DNA molecule. In another embodiment, the polynucleotide is an RNA molecule. A preferred polynucleotide is SEQ ID NO: 1, from nucleotide position 8 to nucleotide position 842.

In another embodiment, a DNA molecule of the present invention is contained in an expression vector. The expression vector preferably further comprises an enhancer-promoter operatively linked to the polynucleotide. In an especially preferred embodiment, the DNA molecule has the nucleotide sequence of SEQ ID NO:1.

In another aspect, the present invention provides an oligonucleotide of from about 15 to about 50 nucleotides containing a nucleotide sequence of at least 15 nucleotides that is identical or complementary to a contiguous sequence of a polynucleotide of this invention. A preferred oligonucleotide is an antisense oligonucleotide that is complementary to a portion of the polynucleotide of SEQ ID NO: 1.

The present invention also provides a pharmaceutical composition comprising an antisense oligonucleotide of this invention and a physiologically acceptable diluent.

In another aspect, the present invention provides an α-tocopherol transport protein of human origin. That α-tocopherol transport protein is an isolated and purified polypeptide of 278 amino acid residues and has the sequence shown in SEQ ID NO:2. Preferably, an α-tocopherol transport protein of the present invention is a recombinant human α-tocopherol transport protein.

In another aspect, the present invention provides a process of making α-tocopherol transport protein comprising transforming a host cell with an expression vector that comprises a polynucleotide of the present invention, maintaining the transformed cell for a period of time sufficient for expression of the α-tocopherol transport protein and recovering the α-tocopherol transport protein. Preferably, the host cell is an eukaryotic host cell such as a human cell, or a bacterial cell. An especially preferred host cell is an *E. coli*. The present invention also provides an α-tocopherol transport protein made by a process of this invention.

The present invention still further provides for a host cell transformed with a polynucleotide or expression vector of this invention. Preferably, the host cell is a bacterial cell such as an *E. coli*.

In another aspect, the present invention provides a process of diagnosing ataxia with vitamin E deficiency. That process comprises detecting the presence of a mutation in the gene for α-tocopherol transport protein, wherein the mutation is (a) a deletion of the thymine at position 485 of exon 3, (b) an insertion of two thymines at position 514 of exon 4 or (c) a substitution of a guanine for an adenine at position 574 of exon 4. In one embodiment of the diagnostic process, the mutation is two or more of (a), (b) and (c).

The detection of mutations can also be used to determine the susceptibility of a child to ataxia with vitamin E deficiency, In accordance with this embodiment, the presence of a mutation in the gene for α-tocopherol transport protein is detected in one or both parents of the child, wherein the mutation is (a) a deletion of the thymine at position 485 of exon 3, (b) an insertion of two thymines at position 514 of exon 4 or (c) a substitution of a guanine for an adenine at position 574 of exon 4.

BRIEF DESCRIPTION OF THE DRAWINGS

In the drawings, which form a portion of the specification:

FIG. 1 shows a full length cDNA clone (SEQ ID NO:1) of α-tocopherol transport protein and a DNA sequence complementary to that clone (SEQ ID NO:3).

FIG. 2 shows the amino acid residue sequence of human (SEQ ID NO:2) and rat (SEQ ID NO:23) α-tocopherol transport protein. Vertical bars connect identical residues between sequences.

DETAILED DESCRIPTION OF THE INVENTION

In one aspect, the present invention provides an isolated and purified polynucleotide that encodes an α-tocopherol transport protein of human origin. A polynucleotide of the present invention that encodes α-tocopherol transport protein is an isolated and purified polynucleotide that comprises a nucleotide sequence consisting essentially of a nucleotide sequence selected from the group consisting of (a) the sequence of SEQ ID NO:1 from nucleotide position 8 to nucleotide position 842, (b) sequences that are complementary to the sequences of (a), and (c) sequences that, when expressed, encode a polypeptide encoded by the sequences of (a). A preferred polynucleotide is a DNA molecule. In another embodiment, the polynucleotide is an RNA molecule.

The nucleotide sequences and deduced amino acid residue sequences of human α-tocopherol transport protein are set forth in FIGS. 1 and 2. The nucleotide sequence of SEQ ID NO:1 in FIG. 1 includes a full length cDNA clone of human α-tocopherol transport protein. SEQ ID NO:2 in FIG. 2 is the deduced amino acid residue sequence of that clone. SEQ ID NO:3 (FIG. 1) is a complementary DNA strand to SEQ ID NO:1.

The present invention also contemplates DNA sequences which hybridize under stringent hybridization conditions to the DNA sequences set forth above. Stringent hybridization conditions are well known in the art and define a degree of sequence identity greater than about 70%–80%. The present invention also contemplates naturally occurring allelic variations and mutations of the DNA sequences set forth above so long as those variations and mutations code, on expression, for an α-tocopherol transport protein of this invention as set forth hereinafter.

As set forth above, SEQ ID NO: 1 is a full length cDNA clone of human α-tocopherol transport protein. As is well known in the art, because of the degeneracy of the genetic code, there are numerous other DNA and RNA molecules that can code for the same polypeptide as that encoded by SEQ ID NO:1. The present invention, therefore, contemplates those other DNA and RNA molecules which, on expression, encode for the polypeptide encoded by SEQ ID NO:1.

Having identified the amino acid residue sequence of α-tocopherol transport protein, and with knowledge of all triplet codons for each particular amino acid residue, it is possible to describe all such encoding RNA and DNA sequences. DNA and RNA molecules other than those specifically disclosed herein and, which molecules are characterized simply by a change in a codon for a particular amino acid are within the scope of this invention.

A Table of codons representing particular amino acids is set forth below in Table 1.

TABLE 1

| First position (5' end) | Second Position | | | | Third position (3' end) |
| --- | --- | --- | --- | --- | --- |
| | T/u | C | A | G | |
| T/U | Phe | Ser | Tyr | Cys | T/U |
| | Phe | Ser | Tyr | Cys | C |
| | Leu | Ser | Stop | Stop | A |
| | Leu | Ser | Stop | Trp | G |
| C | Leu | Pro | His | Arg | T/U |
| | Leu | Pro | His | Arg | C |
| | Leu | Pro | Gln | Arg | A |
| | Leu | Pro | Gln | Arg | G |
| A | Ile | Thr | Asn | Ser | T/U |
| | Ile | Thr | Asn | Ser | C |
| | Ile | Thr | Lys | Arg | A |
| | Met | Thr | Lys | Arg | G |
| G | Val | Ala | Asp | Gly | T/U |
| | Val | Ala | Asp | Gly | C |
| | Val | Ala | Glu | Gly | A |
| | Val | Ala | Glu | Gly | G |

A simple change in a codon for the same amino acid residue within a polynucleotide will not change the structure of the encoded polypeptide. By way of example, it can be seen from SEQ ID NO:1 (see FIG. 1) that a TCA codon for serine exists at nucleotide positions 804–806 and 828–830. It can also be seen from that same sequence, however, that serine can also be encoded by an AGC codon (see e.g., nucleotide positions 834–836). Substitution of the latter AGC codon for serine with the TCT codon for serine, or visa versa, does not substantially alter the DNA sequence of SEQ ID NO:1 and results in expression of the same polypeptide. In a similar manner, substitutions of codons for other amino acid residues can be made in a like manner without departing from the true scope of the present invention.

A polynucleotide of the present invention can also be an RNA molecule. A RNA molecule contemplated by the present invention is complementary to or hybridizes under stringent conditions to any of the DNA sequences set forth above. As is well known in the art, such a RNA molecule is characterized by the base uracil in place of thymine. Exemplary and preferred RNA molecules are mRNA molecules that encode an α-tocopherol transport protein of this invention.

The present invention also contemplates oligonucleotides from about 15 to about 50 nucleotides in length, which oligonucleotides serve as primers and hybridization probes for the screening of DNA libraries and the identification of DNA or RNA molecules that encode α-tocopherol transport protein. Such primers and probes are characterized in that they will hybridize to polynucleotide sequences encoding α-tocopherol transport protein. An oligonucleotide probe or primer contains a nucleotide sequence of at least 15 nucleotides that is identical to or complementary to a contiguous sequence of an α-tocopherol transport protein polynucleotide of the present invention. Thus, where an oligonucleotide probe is 25 nucleotides in length, at least 15 of those nucleotides are identical or complementary to a sequence of contiguous nucleotides of an α-tocopherol transport protein polynucleotide of the present invention. Exemplary α-tocopherol transport protein polynucleotides of the present invention are set forth above.

A preferred oligonucleotide is an antisense oligonucleotide. The present invention provides a synthetic antisense oligonucleotide of less than about 50 nucleotides, preferably less than about 35 nucleotides, more preferably less than about 25 nucleotides and most preferably less than about 20 nucleotides. An antisense oligonucleotide of the present invention is directed against a DNA or RNA molecule that encodes α-tocopherol transport protein. Preferably, the antisense oligonucleotide is directed against the protein translational initiation site or the transcriptional start site.

In accordance with this preferred embodiment, an antisense molecule is directed against a region of SEQ ID NO:1 from about nucleotide position 1 to about nucleotide position 40. It is understood by one of ordinary skill in the art that antisense oligonucleotide can be directed either against a DNA or RNA sequence that encodes a specific target. Thus, an antisense oligonucleotide of the present invention can also be directed against polynucleotides that are complementary to those shown in SEQ ID NO:1 (i.e., SEQ ID NO:3) as well as the equivalent RNA molecules.

Preferably, the nucleotides of an antisense oligonucleotides are linked by pseudophosphate bonds that are resistant to clevage by exonuclease or endonuclease enzymes. Preferably the pseudophosphate bonds are phosphorothioate bonds. By replacing a phosphodiester bond with one that is resistant to the action of exo- and/or endonuclease, the stability of the nucleic acid in the presence of those enzymes is increased. As used herein, pseudophosphate bonds include, but are not limited to, methylphosphonate, phosphomorpholidate, phosphorothioate, phosphorodithioate and phosphoroselenoate bonds.

An oligonucleotide primer or probe, as well as an antisense oligonucleotide of the present invention can be prepared using standard procedures well known in the art. A preferred method of polynucleotide synthesis is via cyanoethyl phosphoramidite chemistry.

An oligonucleotide primer or probe, as well as an antisense oligonucleotide of the present invention can be used for a variety of purposes. An antisense oligonucleotide can be use to inhibit expression the α tocopherol transport protein. An oligonucleotide probe or primer can be used, as is well known in the art, to probe, screen genomic or cDNA libraries to identify nucleic acids that encode related transport proteins. As set forth below, α tocopherol transport protein has significant homology to retinaldehyde binding proteins and phospholipid transport proteins.

A detailed description of the preparation, isolation and purification of polynucleotides encoding human α-tocopherol transport protein is set forth below.

A DNA fragment covering the last 132 base pairs (bp) of the translated region of the rat cDNA αTTP sequence was obtained by PCR from human and rat DNA using primers TTP2 5'CATTGGATGGTVTCAGAATAGCTGCTGA3') (SEQ ID NO:4) and TTP3 (5'CACTTCCCAGACATTCTTCCTCT3')(SEQ ID NO:5). The PCR reaction consisted of 30 cycles of 1 min. at 95% C, 2 min. at 55% C and 1 min. at 73% C preceded by a first denaturation at 95% C for 3 min. The PCR product was run in 1.2% agarose gel and the band was cut out and eluted from the gel by a spin column and then concentrated and purified.

The purified PCR product was then used for PCR labeling using the primers TTP2 and TTP3 for 15 cycles as described above, except that 2 1 1 of α32PdATP was substituted for the cold dATP. This labeled probe was then used to screen 5×105 clones of a human genomic phage library (Stratagene) and the clone pα31 was thus obtained. The direct partial sequence of the phage DNA using primer TTP3 showed high homology to the 3' end of the rat cDNA sequence.

Based on this sequence, a human specific primer HTTP3' (5'TTTAGTTAGGAAGCCATTCACA3')(SEQ ID NO:6) was synthesized from the putative 3' un-translated region. The PCR-labeled fragment using primers TTP3 and HTTP3' and using the phage DNA as template was used to screen a human liver cDNA library. Fourteen positive clones were obtained and their partial sequence showed homologies to the rat cDNA sequence for αTTP. Two clones cTTP9 and cTTP14 were found to contain the full length open reading frame and were sequenced using an automated DNA sequence (ABI). The sequence was partially confirmed by manual cycle sequencing.

The genomic phage clone pα31 originally obtained was found to contain the two last exons by direct sequencing. In order to obtain additional clones spanning the 5' end region of the gene, the full length radio labeled cDNA and a fragment of the cDNA spanning from nucleotide 39 to nucleotide 309, PCR labeled using the cDNA primers VTP2 forward (5'TCAACGCGCTACCGGACCACTCT 3')(SEQ ID NO:7) and primer VTP6 reverse (5'GACTCCATGGTAGCCAGCCTT 3')(SEQ ID NO:8), were used for this screen.

A clone TTPG4 was obtained by screening with the 5' end fragment and three clones, TTPG6, TTPG8 and TTPG9, were obtained using the full length cDNA. The direct partial sequence of the phage TTP6 using primers VTP12 forward (5'GTAGAAACTCAGCGGAATGG 3')(SEQ ID NO:9) and VTP13 reverse (5' CTCCTGTACAATAAGCTCGG 3') (SEQ ID NO:10) which start at position 438 and 437 respectively allowed the identification of the boundaries of exon 3. The direct sequence of the phage DNA from clone TTPG4 using the primers VTP6 and VTP5 forward (5'GCAGATCTACACCCTAGAAGT 3')(SEQ ID NO:11) which starts at nucleotide 253 of the cDNA sequence, allowed us to identify the boundaries of exon 2. Primer VTP18 forward (5'TTCGATCTGGACCTGGCC 3')(SEQ ID NO:12) starting at position 181 of the cDNA sequence was used to identify the junction between exon 1 and intron 1 of the αTTP gene.

To identify the 5' end sequence, a 3.5 EcoR1-Pst1 fragment which contained the 5' end of the αTTP including the first 76 nucleotides of the translated sequence was obtained form phage clone TTPG4 and cloned into puc18 plasmid vector and partially sequences using the plasmid specific primers (A Pst1 site is present in exon 1 at nucleotide position 70–76 of the αTTP cDNA).

The DNA from phages pα31 and HTTPG4 were separately labeled by Biotin-16-dUTP using a multiprime labeling kit (Boehringer). The probe was processed for in situ hybridization using standard procedures well known in the art.

The following primer sets were used to analyze the 5 exons of αTTP.

Exon 1 Set 1
 Forward: Primer VTP2 described above.
 Reverse: 5' GGTCCTGCCTGCACCCT 3' (SEQ ID NO:13)

Exon 1 Set 2
 Forward: 5' GTCCCTAACTAAAGCTGCTAAC 3' (SEQ ID NO:14)
 Reverse: 5! AACGGAGAGTGGTCCGGT 3' (SEQ ID NO:15)

Exon 2
 Forward: 5' CCATGTATGCCATTTGTAGAC 3' (SEQ ID NO:16)
 Reverse: 5' GGGAACACAACTGAACTGGA 3' (SEQ ID NO: 17)

Exon 3
 Forward: 5' CACAATGCTAAGATATGATATGC 3' (SEQ ID NO:18)
 Reverse: 5' GGAAGTATTATGGCTGACAGT 3' (SEQ ID NO:19)

Exon 4
 Forward: 5' ACTTGACATTAGGTATCAGATT 3' (SEQ ID NO:20)
 Reverse: 5' TGTTTGGTGTAGAGGAACAC 3' (SEQ ID NO:21)

Exon 5
 Forward: 5' CATCTAATGCGGTTTCCTTC 3' (SEQ ID NO:22)
 Reverse was primer HTTP3' described above.

Exon 1 was analyzed using two sets of primers because of the extra exonic primers (set 2 forward and set 1 reverse) amplified a large DNA fragment which was not suitable for SSCP analysis. The positions of the primers in the gene sequence of the αTTP gene are indicated in FIG. 3.

Twenty nanograms of patient DNA were amplified by PCR and gel purified as described above. An aliquot of the purified PCR product was used as template for manual cycle sequencing kit (Promega) of both strands using the original PCR primers. Another aliquot of this product was used for cloning into PCRII vector using the TA cloning procedure (Invitrogen). The plasmid DNA from exon 3 was manually sequenced by cycle sequencing using the original PCR primers and the cDNA forward primer VTP12.

Fourteen overlapping cDNA clones were obtained and partially or fully sequenced. A full open reading frame encoding 278 amino acids was obtained. This sequence was deposited in Genbank under accession # U21938. The nucleotide sequence has 84% homology to the rat cDNA sequence.

The analysis of the somatic cell hybrid panel (Bios., Connecticut) showed 100% concordance for the mapping of αTTP to chromosome 8. Over 50 meiosis in the fluorescent in situ hybridization were analyzed. The signal was seen on chromosome 8q13 in most instances, which established the location of the human αTTP to chromosome 8q13.

The analysis and partial direct sequence of DNA from phages pα31, TTPG4 and TTPG6 showed the human αTTP gene to be composed of 5 exons. The intron-exon junctions of the two last exons were obtained by direct partial sequence of the DNA from phages clone pα31, the exon-intron junctions of the first two exons were obtained by direct sequence of the phage TTPG4, while the boundaries of exon 3 were obtained form phage TTPG6. The sequence of the CG rich 5' end of the gene was obtained form the 3.5 KB ECOR1-PST1 subclone from the phage clone TTPG4. Phage clones pα31, TTPG4 and TTPG6 were obtained using a 3' end, 5' end and full length cDNA probes respectively. All the exon-intron junctions in αTTP gene respond to the AG . . . GT rule.

In another aspect, the present invention provides an α-tocopherol transport protein of human origin. An α-tocopherol transport protein of the present invention is a polypeptide of 278 amino acid residues (SEQ ID NO:2).

The amino acid sequence has 87% identity to the rat sequence for αTTP (SEQ ID NO:23 of FIG. 2). Homology of the amino acid sequence was observed between αTTP and human and bovine cellular retinaldehyde binding proteins (Genbank acc. Nos. B311955 and P1227 respectively). The human αTTP also showed homology to phosphatidylinositol/phosphatidyl choline transfer protein from yeast (Genbank acc. No. S43745). This strongly suggests that these proteins belong to a distinct family involved in the transport of lipophilic molecules.

The present invention also contemplates amino acid residue sequences that are substantially duplicative of the sequences set forth herein such that those sequences demonstrate like biological activity to disclosed sequences. Such contemplated sequences include those sequences characterized by a minimal change in amino acid residue sequence or type (e.g., conservatively substituted sequences) which insubstantial change does not alter the basic nature and biological activity of α-tocopherol transport protein.

It is well known in the art that modifications and changes can be made in the structure of a polypeptide without substantially altering the biological function of that peptide. For example, certain amino acids can be substituted for other amino acids in a given polypeptide without any appreciable loss of function. In making such changes, substitutions of like amino acid residues can be made on the basis of relative similarity of side-chain substituents, for example, their size, charge, hydrophobicity, hydrophilicity, and the like.

As detailed in U.S. Pat. No. 4,554,101, incorporated herein by reference, the following hydrophilicity values have been assigned to amino acid residues: Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4). It is understood that an amino acid residue can be substituted for another having a similar hydrophilicity value (e.g., within a value of plus or minus 2.0) and still obtain a biologically equivalent polypeptide.

In a similar manner, substitutions can be made on the basis of similarity in hydropathic index. Each amino acid residue has been assigned a hydropathic index on the basis of its hydrophobicity and charge characteristics. Those hydropathic index values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). In making a substitution based on the hydropathic index, a value of within plus or minus 2.0 is preferred.

An α-tocopherol transport protein polypeptide of the present invention has numerous uses. By way of example, such a polypeptide can be used in a screening assay for the identification of drugs or compounds that inhibit the action of α-tocopherol transport protein (e.g., agonist and antagonist).

An α-tocopherol transport protein can also be used therapeutically. As set forth above, α-tocopherol transport protein functions to enhance the transport of vitamin E across cell membranes. The administration of α-tocopherol transport protein, therefore, can be used to enhance vitamin E uptake into cells and, particularly, liver cells. The levels of vitamin E inside those cells can be even further increased by co-administering vitamin E along with the α-tocopherol transport protein. As set forth hereinafter, the protein is typically delivered in a pharmaceutical composition having a variety of formulations. Particularly suitable formulations for enhancing vitamin E uptake are liposomes. The delivery of α-tocopherol transport protein can be targeted to particular cell types, as is well kwon in the art, by conjugating the protein to a targeting moiety such as an antibody that has immunospecificity for a cell surface antigen on the target cell.

The use of α-tocopherol transport protein to enhance vitamin E uptake on intracellular levels is particularly useful in treating disorder associated with oxygen free radicals. As is well known in the art, vitamin E is an effective free radical scavenger. Increasing the levels of vitamin E, therefore, is useful for imposing resistance to antioxidants.

In addition, an α-tocopherol transport protein polypeptide of the present invention can be used to produce antibodies that immunoreact specifically with α-tocopherol transport protein. Means for producing antibodies are well known in the art. An antibody directed against α-tocopherol transport protein can be a polyclonal or a monoclonal antibody.

Antibodies against α-tocopherol transport protein can be prepared by immunizing an animal with an α-tocopherol transport protein polypeptide of the present invention. Means for immunizing animals for the production of antibodies are well known in the art. By way of an example, a mammal can be injected with an inoculum that includes a polypeptide as described herein above. The polypeptide can be included in an inoculum alone or conjugated to a carrier protein such as keyhole limpet hemocyanin (KLH). The polypeptide can be suspended, as is well known in the art, in an adjuvant to enhance the immunogenicity of the polypeptide. Sera containing immunologically active antibodies are then produced from the blood of such immunized animals using standard procedures well known in the art.

The identification of antibodies that immunoreact specifically with α-tocopherol transport protein is made by exposing sera suspected of containing such antibodies to a polypeptide of the present invention to form a conjugate between antibodies and the polypeptide. The existence of the conjugate is then determined using standard procedures well known in the art.

An α-tocopherol transport protein polypeptide of the present invention can also be used to prepare monoclonal antibodies against α-tocopherol transport protein and used as a screening assay to identify such monoclonal antibodies. Monoclonal antibodies are produced from hybridomas prepared in accordance with standard techniques such as that described by Kohler et al. (*Nature*, 256:495, 1975). Briefly, a suitable mammal (e.g., BALB/c mouse) is immunized by injection with a polypeptide of the present invention. After a predetermined period of time, splenocytes are removed from the mouse and suspended in a cell culture medium. The splenocytes are then fused with an immortal cell line to form a hybridoma. The formed hybridomas are grown in cell culture and screened for their ability to produce a monoclonal antibody against α-tocopherol transport protein. Screening of the cell culture medium is made with a polypeptide of the present invention.

In another aspect, the present invention provides a process of making α-tocopherol transport protein. In accordance with that process, a suitable host cell is transformed with a polynucleotide of the present invention. The transformed cell is maintained for a period of time sufficient for expression of the α-tocopherol transport protein. The formed α-tocopherol transport protein is then recovered.

Means for transforming host cells in a manner such that those cells produce recombinant polypeptides are well known in the art. Briefly, a polynucleotide that encodes the desired polypeptide is placed into an expression vector suitable for a given host cell. That vector can be a viral vector, phage or plasmid. In a preferred embodiment, a host cell used to produce α-tocopherol transport protein is an eukaryotic host cell and an expression vector is an eukaryotic expression vector (i.e., a vector capable of directing expression in a eukaryotic cell). Such eukaryotic expression vectors are well known in the art.

In another preferred embodiment, the host cell is a bacterial cell. An especially preferred bacterial cell is an *E. coli*. Thus, a preferred expression vector is a vector capable of directing expression in *E. coli*.

A polynucleotide of an expression vector of the present invention is preferably operatively associated or linked with an enhancer-promoter. A promoter is a region of a DNA molecule typically within about 100 nucleotide pairs in front of (upstream of) the point at which transcription begins. That region typically contains several types of DNA sequence elements that are located in similar relative positions in different genes. As used herein, the term "promoter" includes what is referred to in the art as an upstream promoter region or a promoter of a generalized RNA polymerase transcription unit.

Another type of transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from a transcription start site so long as the promoter is present.

As used herein, the phrase "enhancer-promoter" means a composite unit that contains both enhancer and promoter elements. An enhancer promoter is operatively linked to a coding sequence that encodes at least one gene product. As used herein, the phrase "operatively linked" or its grammatical equivalent means that a regulatory sequence element (e.g. an enhancer-promoter or transcription terminating region) is connected to a coding sequence in such a way that the transcription of that coding sequence is controlled and regulated by that enhancer-promoter. Means for operatively linking an enhancer-promoter to a coding sequence are well known in the art.

An enhancer-promoter used in an expression vector of the present invention can be any enhancer-promoter that drives expression in a host cell. By employing an enhancer-promoter with well known properties, the level of expression can be optimized. For example, selection of an enhancer-promoter that is active in specifically transformed cells permits tissue or cell specific expression of the desired product. Still further, selection of an enhancer-promoter that is regulated in response to a specific physiological signal can permit inducible expression.

A coding sequence of an expression vector is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA). Enhancer-promoters and transcription-terminating regions are well known in the art. The selection of a particular enhancer-promoter or transcription-terminating region will depend, as is also well known in the art, on the cell to be transformed.

An expression vector of the present invention has particular utility as a means of increasing vitamin E uptake and intracellular vitamin E levels in target cells. A particular target cell is transformed with an expression vector containing a polynucleotide that encodes α-tocopherol transport protein. Expression of that protein inside the cell enhances the transmembrane uptake of vitamin E and thus, the intracellular levels of that vitamin. Transformation of target cells can occur using ex vivo procedures, whereby cells are removed from the body transformed in vitro and then re-transplanted into the body. Alternatively, transformation of the target cells can occur in vivo. Preferred expression vectors for in vivo transformation are viral vectors such as retroviral vectors and adenoviral vectors. The use of such viral vectors for transformation is well known in the art.

The present invention also contemplates a host cell transformed with a polynucleotide or expression vector of this invention. Means for transforming cells and polynucleotides and expression vectors used to transform host cells are set forth above. Preferably, the host cell is an eukaryotic host cell such as a human cell or a prokaryotic cell such as an *E. coli*.

The present invention also provides a pharmaceutical composition comprising a polypeptide or a polynucleotide of this invention and a physiologically acceptable diluent.

In a preferred embodiment, the present invention includes one or more antisense oligonucleotides or polypeptides, as set forth above, formulated into compositions together with one or more non-toxic physiologically tolerable or acceptable diluents, carriers, adjuvants or vehicles that are collectively referred to herein as diluents, for parenteral injection, for oral administration in solid or liquid form, for rectal or topical administration, or the like.

The compositions can be administered to humans and animals either orally, rectally, parenterally, intracisternally, intravaginally, intraperitoneally, locally, or as a buccal or nasal spray.

Compositions suitable for parenteral administration can comprise physiologically acceptable sterile aqueous or non-aqueous solutions, dispersions, suspensions or emulsions and sterile powders for reconstitution into such sterile solutions or dispersions. Examples of suitable diluents include water, ethanol, polyols, suitable mixtures thereof, vegetable oils and injectable organic esters such as ethyl oleate. Proper fluidity can be maintained, for example, by the use of a coating such as lecithin, by the maintenance of the required particle size in the case of dispersions and by the use of surfactants.

Compositions can also contain adjuvants such as preserving, wetting, emulsifying, and dispensing agents. Prevention of the action of microorganisms can be insured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form can be brought about by the use of agents delaying absorption, for example, aluminum monostearate and gelatin.

Besides such inert diluents, the composition can also include sweetening, flavoring and perfuming agents. Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonit, agar-agar and tragacanth, or mixtures of these substances, and the like.

In another aspect, the present invention provides a process of diagnosing ataxia with vitamin E deficiency. That process comprises detecting the presence of a mutation in the gene for α-tocopherol transport protein, wherein the mutation is (a) a deletion of the thymine at position 485 of exon 3, (b) an insertion of two thymines at position 514 of exon 4 or (c) a substitution of a guanine for an adenine at position 574 of exon 4. In one embodiment of the diagnostic process, the mutation is two or more of (a), (b) and (c).

The detection of mutations can also be used to determine the susceptibility of a child to ataxia with vitamin E deficiency, In accordance with this embodiment, the presence of a mutation in the gene for α-tocopherol transport protein is detected in one or both parents of the child, wherein the mutation is (a) a deletion of the thymine at position 485 of exon 3, (b) an insertion of two thymines at position 514 of exon 4 or (c) a substitution of a guanine for an adenine at position 574 of exon 4.

Three patients with AVED from three unrelated North American families of Caucasian descent have been analyzed. Patients 1707 and 950433 were isolated cases, while patient 1806 belongs to a sibship of three affected individuals. The clinical findings of these patients are summarized in Table 2 below.

TABLE 2

| | Patient # | | |
|---|---|---|---|
| | 1707 | 1806 | 950433 |
| Age of onset of symptoms (years) | 3 | 6 | 7 |
| Age at inability to walk (years) | 20 | No | 17 |
| Clinical Symptoms | | | |
| Ataxia | + | + | + |
| Dysarthrya | + | − | + |
| Hyporeflexia | + | − | + |
| Vibratory sense loss | + | + | + |
| Position sense loss | + | − | + |
| Plantar response | extensor | − | extensor |
| Mental status | Normal | Normal | Normal |
| Other symptoms | − | − | dystonic posturing |

All of the exons of αTTP were tested by single strand conformation polymorphism (SSCP) analysis. SSCP changes were observed as band shifts of the PCR amplified DNA from exon 3 in patients 1707 and 950433 and in both of their parents as well as in patient 1806.

The SSCP pattern of exon 3 in patient 1806 and the two parents of patient 1707 were identical, while the pattern for patient 1707 suggested a monozygous mutation. The SSCP patterns of exon 3 from patient 950433 and his parents were different from those observed in patients 1707 and 1806, and suggested a mutation with which the patient was homozygous and his parents were heterozygous. Patient 1806 was compound heterozygous as her DNA had an SSCP change in exon 4. The direct sequence of the PCR product of exon 3 from patient 1707 showed a homozygous insertion of TT at position 514. This mutation was verified by sequencing two clones of the cloned PCR product. Four clones of the cloned PCR product of exon 3 from patient 1806 were also sequenced. Two clones showed the normal sequence, while the two remaining clones showed the TT insertion at the same position as individual 1707 confirming that patient 1806 was heterozygote with this mutation.

The direct sequencing of the PCR product of exon 3 from patient 950433 and both parents showed that this patient was homozygous for a deletion of the T at position 485 (485delT) while both parents were heterozygous for this mutation. Both mutations 513instTT and 485delT cause a frame shift and would create a truncated αTTP of 175 amino acids long including four additional aberrant amino acids (Leu-Leu-His-Pro; SEQ ID NO:24) with 513insTT and 12 aberrant amino acids (Gly-Ser-Phe-Leu-Met-Leu-Phe-Lys-Ser-Leu-His-Pro; SEQ ID NO:25) with 485delT. The direct sequence of the PCR product of exon 4 from patient 1806 showed a heterozygote mutation substituting A to G at position 574 which would replace the arginine 192 in the wild type αTTP to histidine. The arginine 192 residue was conserved in the rat sequence and in more than 100 chromosomes from unrelated individuals of North American origin as determined by SSCP analysis. The analysis of exons, 1, 2 and 5 of αTTP did not show any SSCP change.

A common SSCP change with a different pattern than the change observed in patient 1806 was observed using exon 4 primers. This SSCP change resulted from a T-C polymorphism at position 11 of intron 4, as shown by the sequence of the PCR products from individuals homozygous and heterozygous with this polymorphism. The frequency of allele T in the Caucasian population is 0.66.

The mutation 5134instTT and 485delT are expected to truncate 38% and 42% of the protein respectively and are likely to severely alter the α-tocopherol transfer function of the protein. These mutations were observed in the homozygote state in patients 1707 and 950433 who presented with a severe form of AVED. Patient 1806 was compound heterozygote and had both 513insTT and the Arg192->His substitution. A mutation has been recently reported in presumably this patient's family as a TG insertion, which is different from our observation, and none of the mutations 485delT and 574 G->A were previously reported. The AVED phenotype in patient 1806 is most likely due to the combination of the 513insTT mutation and the Arg1932->His substitution. This latter mutation involves a conserved residue between human and rat sequences and was not found in the control population analyzed. It is possible that some residual activity of αTTP with Arg192->His substitution persists since the symptoms of AVED were milder in this family than in patients 1707 and 950433.

These data demonstrate the involvement of αTTP in the AVED phenotype. The mechanism by which vitamin E deficiency causes neurodegeneration is unknown. The only accepted function of vitamin E in humans is its role as scavenger of free radicals and the lack of this function may be the cause of neurodegeneration. A related mechanism of neurodegeneration has been suggested in familial amyothrophic lateral sclerosis (FALS) with mutations in the Cu/Zn superoxide dismutase (a major antioxidant cellular defense) which result in reduced dismutase activity. Although phenotypically, AVED (a central and peripheral axonopathy) and FALS (a motor neuron degeneration) are distinct, the underlying mechanism in both disorders suggests an impairment of antioxidant defense which may lead to an increase in ambient free radicals. Damage caused by free radicals may interfere with neuronal repair and maintenance and could lead to neurodegeneration.

The present invention also contemplates transgenic non-human animals whose germ cells contain a transgene for α tocopherol transport protein. The phrase "non-human animals" comprises any non-human animal having an immune system capable of producing a humoral and/or cell-mediated immune response. Exemplary non-human animals include vertebrates such as rodent, non-human primates, sheep, dog, cow, amphibians, reptiles, etc. Preferred non-human animals are selected from the rodent family including rat and mouse, most preferably mouse.

As is well known in the art, transgenic non-human animals are produced by introducing "transgenes" into the germine of the non-human animal. By way of example, embryonal target cells at various developmental stages can be used. The zygote is the preferred target for microinjection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage. As a consequence, all cells of the transgenic non-human animal carry the incorporated transgene. Efficient transmission of the transgene to offspring of the founder occurs because 50% of the germ cells harbor the transgene. Microinjection of zygotes is the preferred method for incorporating transgenes in practicing the invention.

Retroviral infection can also be used to introduce transgene into a non-human animal. The developing non-human embryo can be cultured in vitro to the blastocyst stage. Efficient infection of the blastomeres is obtained by enzymatic treatment to remove the zona pellucida. The viral vector system used to introduce the transgene is typically a replication-defective retrovirus carrying the transgene Transfection is easily and efficiently obtained by culturing the blastomeres on a monolayer of virus-producing cells. Alternatively, infection can be performed at a later stage. Virus or virus-producing cells can be injected into the blastocoele. Most of the founders are mosaic for the transgene because incorporation occurs only in a subset of the cells which formed the transgenic non-human animal. In addition, it is also possible to introduce transgenes into the germ line, albeit with low efficiency, by intrauterine retroviral infection of the midgestation embryo.

Another type of target cell for transgene introduction is the embryonal stem cell (ES). ES cells are obtained from pre-implantation embryos cultures in vitro and fused with embryos. Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. As used herein, a "transgene" is a DNA sequence introduced into the germline of a non-human animal by way of human intervention such as by way of the above described methods.

The mutation 513insTT and 485delT are expected to truncate 38% and 42% of the protein respectively and are likely to severely alter the α-tocopherol transfer function of the protein. These mutations were observed in the homozygote state in patients 1707 and 950433 who presented with a severe form of AVED. (Table 2). Patient 1806 was compound heterozygote and had both 513insTT and the Arg192->His substitution. A mutation has been recently reported in presumably this patient's family as a TG insertion which is different from our observation, and none of the mutations 485delT and 574 G->A were previously reported. The AVED phenotype in patient 1806 is most likely due to the combination of the 513insTT mutation and the Arg1932->His substitution. This latter mutation involves a conserved residue between human and rat sequences and was not found in the control population analyzed. It is possible that some residual activity of αTTP with Arg192->His substitution persists since the symptoms of AVED were milder in this family than in patients 1707 and 950433 (Table 2). The effect of the Arg92->His substitution on the tertiary structure of the αTTP cannot be determined because the crystallographic structure of αTTP has not been solved.

The invention has now been described with reference to preferred embodiments. Those embodiments are not limiting of the specification or claims in any way.

What is claimed is:

1. An isolated and purified polypeptide having the amino acid residue sequence of SEQ ID NO:2.

2. A process of detecting an antibody against α-tocopherol transport protein in a biological sample comprising adding the polypeptide of claim 1 to a biolgical sample, maintaining the sample for a period of time sufficient for formation of a conjugate between the antibody and the polypeptide and detecting the presence of the conjugate and thereby the antibody.

3. A recombinant human α-tocopherol transport protein having the amino acid sequence of SEQ IN NO:2 or having the amino acid sequence of SEQ ID NO:2 which contains one or more amino acid substitutions and retains α-tocopherol transport activity wherein an amino acid is substituted for another amino acid having a hydrophilicity value within a value of plus or minus 2.0 or a hydropathic index value with plus or minus 2.0 or wherein an amino acid is conservatively substituted.

4. A pharmaceutical composition comprising the polypeptide of claim 3 and a physiologically acceptable diluent.

5. An isolated and purified polynucleotide comprising a nucleotide sequence consisting of the sequence of SEQ ID NO:1 from nucleotide position 8 to nucleotide position 842; a sequence that is complementary to SEQ ID NO:1 from nucleotide position 8 to nucletide position 842 or a sequence that, on expression, encodes a polypeptide encoded by SEQ ID NO: 1 from nucleotide position 8 to nucleotide position 842.

6. The polynucleotide of claim 5 that is an RNA molecule.

7. The polynucleotide of claim 5 that is a DNA molecule.

8. The polynucleotide of claim 7 having the nucleotide sequence SEQ ID NO:1.

9. An expression vector comprising the DNA molecule of claim 7.

10. The expression vector of claim 9 wherein the polynucleotide has the nucleotide sequence of SEQ ID NO: 1 from nucleotide position 8 to nucleotide position 842.

11. The expression vector of claim 9 further comprising an enhancer-promoter operatively linked to the polynucleotide.

12. A host cell transformed with the expression vector of claim 9.

13. A process of making α-tocopherol transport protein comprising transforming a host cell with the expression vector of claim 9, maintaining the transformed cell for a period of time sufficient for expression of the protein and recovering the protein.

* * * * *

UNITED STATES PATENT AND TRADEMARK OFFICE
CERTIFICATE OF CORRECTION

PATENT NO. : 6,268,170 B1
DATED : July 31, 2001
INVENTOR(S) : Siddique et al.

It is certified that error appears in the above-identified patent and that said Letters Patent is hereby corrected as shown below:

Column 1,
Before line 1, please insert -- The research for the invention disclosed herein was supported by NIH Grant No.: NS-21442 and NIH Grant No.: NS-31248. The United States Government may own certain rights to the invention disclosed herein. --

Column 2,
Line 30, please delete "deficiency," and insert -- deficiency. --

Column 4,
Line 7, please delete "such a" and insert -- such an --

Column 5,
Line 2, please delete "be use" and insert -- be used --

Column 6,
Line 28, please delete "5!" and insert -- 5' --

Column 7,
Line 17, please delete "form" and insert -- from --

Column 8,
Line 29, please delete "kwon" and insert -- known --

Column 13,
Line 25, please delete "germine" and insert -- germline --

UNITED STATES PATENT AND TRADEMARK OFFICE
CERTIFICATE OF CORRECTION

PATENT NO. : 6,268,170 B1
DATED : July 31, 2001
INVENTOR(S) : Siddique et al.

It is certified that error appears in the above-identified patent and that said Letters Patent is hereby corrected as shown below:

Column 14,
Line 42, please delete "Arg92->" and insert -- Arg192-> --

Column 29,
Line 36, please delete "SEQ IN NO:2" and insert -- SEQ ID NO:2 --

Signed and Sealed this

Sixteenth Day of April, 2002

Attest:

JAMES E. ROGAN
*Director of the United States Patent and Trademark Office*

*Attesting Officer*

UNITED STATES PATENT AND TRADEMARK OFFICE
CERTIFICATE OF CORRECTION

PATENT NO. : 6,268,170 B1 Page 1 of 1
APPLICATION NO. : 08/557614
DATED : July 31, 2001
INVENTOR(S) : Siddique et al.

It is certified that error appears in the above-identified patent and that said Letters Patent is hereby corrected as shown below:

Column 1, before line 1, please delete

"The research for the invention disclosed herein was supported by NIH Grant No.: NS-21442 and NIH Grant No.: NS-31248. The United States Government may own certain rights to the invention disclosed herein."

and insert

-- This invention was made with government support under Grant Numbers P50-NS-21442-09A1 and P01-NS-31248 awarded by the National Institutes of Health. The government has certain rights in the invention. --

Signed and Sealed this

Thirtieth Day of June, 2009

JOHN DOLL
*Acting Director of the United States Patent and Trademark Office*

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 915 base pairs
      (B) TYPE: nucleic acid
      (C) STRANDEDNESS: single
      (D) TOPOLOGY: linear (ii) MOLECULE TYPE: cDNA (ix) FEATURE:

-continued

```
        (A) NAME/KEY: CDS
        (B) LOCATION: 8..845

(ix) FEATURE:
        (A) NAME/KEY: mat_peptide
        (B) LOCATION: 8..842

(xi) SEQUENCE DESCRIPTION: SEQ ID NO:1:

GGCGGGC ATG GCA GAG GCG CGA TCC CAG CCC TCG GCG GGG CCG CAG CTC          49
        Met Ala Glu Ala Arg Ser Gln Pro Ser Ala Gly Pro Gln Leu
        1               5                  10

AAC GCG CTA CCG GAC CAC TCT CCG TTG CTG CAG CCG GGC CTG GCG GCG          97
Asn Ala Leu Pro Asp His Ser Pro Leu Leu Gln Pro Gly Leu Ala Ala
15                  20                  25                  30

CTG CGG CGC CGG GCC CGG GAA GCT GGC GTC CCG CTC GCG CCG CTG CCG         145
Leu Arg Arg Arg Ala Arg Glu Ala Gly Val Pro Leu Ala Pro Leu Pro
                35                  40                  45

CTC ACC GAC TCC TTC CTG CTG CGG TTC CTG CGC GCC CGG GAT TTC GAT         193
Leu Thr Asp Ser Phe Leu Leu Arg Phe Leu Arg Ala Arg Asp Phe Asp
            50                  55                  60

CTG GAC CTG GCC TGG CGG TTA CTA AAA AAC TAT TAT AAG TGG AGA GCA         241
Leu Asp Leu Ala Trp Arg Leu Leu Lys Asn Tyr Tyr Lys Trp Arg Ala
        65                  70                  75

GAA TGT CCA GAA ATA AGT GCA GAT CTA CAC CCT AGA AGT ATT ATT GGC         289
Glu Cys Pro Glu Ile Ser Ala Asp Leu His Pro Arg Ser Ile Ile Gly
    80                  85                  90

CTC CTA AAG GCT GGC TAC CAT GGA GTC CTG AGA TCC AGG GAT CCC ACT         337
Leu Leu Lys Ala Gly Tyr His Gly Val Leu Arg Ser Arg Asp Pro Thr
95                  100                 105                 110

GGC AGC AAA GTT CTT ATT TAC AGA ATC GCA CAC TGG GAC CCC AAA GTT         385
Gly Ser Lys Val Leu Ile Tyr Arg Ile Ala His Trp Asp Pro Lys Val
                115                 120                 125

TTT ACA GCT TAT GAC GTA TTT CGA GTA AGT CTA ATC ACA TCC GAG CTT         433
Phe Thr Ala Tyr Asp Val Phe Arg Val Ser Leu Ile Thr Ser Glu Leu
            130                 135                 140

ATT GTA CAG GAG GTA GAA ACT CAG CGG AAT GGA ATC AAG GCT ATC TTT         481
Ile Val Gln Glu Val Glu Thr Gln Arg Asn Gly Ile Lys Ala Ile Phe
        145                 150                 155

GAT CTG GAA GGT TGG CAG TTT TCT CAT GCT TTT CAA ATC ACT CCA TCC         529
Asp Leu Glu Gly Trp Gln Phe Ser His Ala Phe Gln Ile Thr Pro Ser
    160                 165                 170

GTA GCC AAG AAG ATT GCT GCT GTA CTT ACG GAT TCA TTT CCA TTG AAA         577
Val Ala Lys Lys Ile Ala Ala Val Leu Thr Asp Ser Phe Pro Leu Lys
175                 180                 185                 190

GTT CGT GGC ATC CAT TTG ATA AAT GAA CCA GTA ATT TTC CAT GCT GTC         625
Val Arg Gly Ile His Leu Ile Asn Glu Pro Val Ile Phe His Ala Val
                195                 200                 205

TTT TCC ATG ATC AAA CCA TTC CTG ACT GAA AAA ATT AAG GAA CGG ATT         673
Phe Ser Met Ile Lys Pro Phe Leu Thr Glu Lys Ile Lys Glu Arg Ile
            210                 215                 220

CAC ATG CAT GGG AAC AAC TAC AAA CAA AGC TTG CTT CAG CAT TTC CCA         721
His Met His Gly Asn Asn Tyr Lys Gln Ser Leu Leu Gln His Phe Pro
        225                 230                 235

GAC ATT CTT CCT CTG GAA TAT GGT GGT GAA GAA TTC TCC ATG GAG GAC         769
Asp Ile Leu Pro Leu Glu Tyr Gly Gly Glu Glu Phe Ser Met Glu Asp
    240                 245                 250

ATT TGT CAG GAA TGG ACA AAT TTT ATA ATG AAG TCT GAA GAT TAT CTC         817
Ile Cys Gln Glu Trp Thr Asn Phe Ile Met Lys Ser Glu Asp Tyr Leu
255                 260                 265                 270

AGG AGC ATT TCT GAG AGC ATT CAA TGA G AAGTTATGTC ATGTGAATGG             865
Arg Ser Ile Ser Glu Ser Ile Gln
```

```
                275
CTTCCTAACT AAAATCATGA GTGATATCCA ACTGGTTAAT TGATTGAAGA                     915
```

(2) INFORMATION FOR SEQ ID NO:2:

(i) SEQUENCE CHARACTERISTICS:
        (A) LENGTH: 278 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Glu Ala Arg Ser Gln Pro Ser Ala Gly Pro Gln Leu Asn Ala
 1               5                  10                  15

Leu Pro Asp His Ser Pro Leu Leu Gln Pro Gly Leu Ala Ala Leu Arg
             20                  25                  30

Arg Arg Ala Arg Glu Ala Gly Val Pro Leu Ala Pro Leu Pro Leu Thr
         35                  40                  45

Asp Ser Phe Leu Leu Arg Phe Leu Arg Ala Arg Asp Phe Asp Leu Asp
     50                  55                  60

Leu Ala Trp Arg Leu Leu Lys Asn Tyr Tyr Lys Trp Arg Ala Glu Cys
 65                  70                  75                  80

Pro Glu Ile Ser Ala Asp Leu His Pro Arg Ser Ile Ile Gly Leu Leu
                 85                  90                  95

Lys Ala Gly Tyr His Gly Val Leu Arg Ser Arg Asp Pro Thr Gly Ser
            100                 105                 110

Lys Val Leu Ile Tyr Arg Ile Ala His Trp Asp Pro Lys Val Phe Thr
        115                 120                 125

Ala Tyr Asp Val Phe Arg Val Ser Leu Ile Thr Ser Glu Leu Ile Val
    130                 135                 140

Gln Glu Val Glu Thr Gln Arg Asn Gly Ile Lys Ala Ile Phe Asp Leu
145                 150                 155                 160

Glu Gly Trp Gln Phe Ser His Ala Phe Gln Ile Thr Pro Ser Val Ala
                165                 170                 175

Lys Lys Ile Ala Ala Val Leu Thr Asp Ser Phe Pro Leu Lys Val Arg
            180                 185                 190

Gly Ile His Leu Ile Asn Glu Pro Val Ile Phe His Ala Val Phe Ser
        195                 200                 205

Met Ile Lys Pro Phe Leu Thr Glu Lys Ile Lys Glu Arg Ile His Met
    210                 215                 220

His Gly Asn Asn Tyr Lys Gln Ser Leu Leu Gln His Phe Pro Asp Ile
225                 230                 235                 240

Leu Pro Leu Glu Tyr Gly Gly Glu Glu Phe Ser Met Glu Asp Ile Cys
                245                 250                 255

Gln Glu Trp Thr Asn Phe Ile Met Lys Ser Glu Asp Tyr Leu Arg Ser
            260                 265                 270

Ile Ser Glu Ser Ile Gln
        275
```

(2) INFORMATION FOR SEQ ID NO:3:

(i) SEQUENCE CHARACTERISTICS:
        (A) LENGTH: 913 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

| | | | | | |
|---|---|---|---|---|---|
| CCGCCCGTAC | CGTCTCCGCG | CTAGGGTCGG | GAGCCGCCCC | GGCGTCGAGT | TGCGCGATGG | 60 |
| CCTGGTGAGA | GGCAACGACG | TCGGCCCGGA | CCGCCGCGAC | GCCGCGGCCC | GGGCCCTTCG | 120 |
| ACCGCAGGGC | GAGCGCGGCG | ACGGCGAGTG | GCTGAGGAAG | GACGACGCCA | AGGACGCGCG | 180 |
| GGCCCTAAAG | CTAGACCTGG | ACCGGACCGC | CAATGATTTT | TTGATAATAT | TCACCTCTCG | 240 |
| TCTTACAGGT | CTTTATTCAC | GTCTAGATGT | GGGATCTTCA | TAATAACCGG | AGGATTTCCG | 300 |
| ACCGATGGTA | CCTCAGGACT | CTAGGTCCCT | AGGGTGACCG | TCGTTTCGAA | TAAATGTCTT | 360 |
| AGCGTGTGAC | CCTGGGGTTT | CAAAAATGTC | GAATACTGCA | TAAAGCTCAT | TCAGATTAGT | 420 |
| GTAGGCTCGA | ATAACATGTC | CTCCATCTTT | GAGTCGCCTT | ACCTTAGTTC | CGATAGAAAC | 480 |
| TAGACCTTCC | AACCGTCAAA | AGAGTACGAA | AAGTTTAGTG | AGGTAGGCAT | CGGTTCTTCT | 540 |
| AACGACGACA | TGAATGCCTA | AGTAAAGGTA | ACTTTCAAGC | ACCGTAGGTA | AACTATTTAC | 600 |
| TTGGTCATTA | AAAGGTACGA | CAGAAAAGGT | ACTAGTTTGG | TAAGGACTGA | CTTTTTTAAT | 660 |
| TCCTTGCCTA | AGTGTACGTA | CCCTTGTTGA | TGTTTGTTTC | GAACGAAGTC | GTAAAGGGTC | 720 |
| TGTAAGAAGG | AGACCTTATA | CCACCACTTC | TTAAGAGGTA | CCTCCTGTAA | ACAGTCCTTA | 780 |
| CCTGTTTAAA | ATATTACTTC | AGACTTCTAA | TAGAGTCCTC | GTAAAGACTC | TCGTAAGTTA | 840 |
| CTCTTCAATA | CAGTACACTT | ACCGAAGGAT | TGATTTTAGT | ACTCACTATA | GGTTGACCAA | 900 |
| TTAACTAACT | TCT | | | | | 913 |

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CATTGGATGG TTCAGAATAG CTGCTGA  27

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CACTTCCCAG ACATTCTTCC TCT  23

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
TTTAGTTAGG AAGCCATTCA CA                                              22

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TCAACGCGCT ACCGGACCAC TCT                                             23

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GACTCCATGG TAGCCAGCCT T                                               21

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GTAGAAACTC AGCGGAATGG                                                 20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CTCCTGTACA ATAAGCTCGG                                                 20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CTCCTGTACA ATAAGCTCGG                                                 20

(2) INFORMATION FOR SEQ ID NO:12:
```

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:12:

TTCGATCTGG ACCTGGCC                                              18

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GGTCCTGCCT GCACCCT                                               17

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GTCCCTAACT AAAGCTGCTA AC                                         22

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

AACGGAGAGT GGTCCGGT                                              18

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

CCATGTATGC CATTTGTAGA C                                          21

(2) INFORMATION FOR SEQ ID NO:17:

(i) SEQUENCE CHARACTERISTICS:
        (A) LENGTH: 20 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:17:

GGGAACACAA CTGAACTGGA                                               20

(2) INFORMATION FOR SEQ ID NO:18:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

CACAATGCTA AGATATGATA TGC                                           23

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

GGAAGTATTA TGGCTGACAG T                                             21

(2) INFORMATION FOR SEQ ID NO:20:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

ACTTGACATT AGGTATCAGA TT                                            22

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

TGTTTGGTGT AGAGGAACAC                                               20

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:22:

CATCTAATGC GGTTTCCTTC                                                                            20

(2) INFORMATION FOR SEQ ID NO:23:

(i) SEQUENCE CHARACTERISTICS:
        (A) LENGTH: 278 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Met Ala Glu Met Arg Pro Gly Pro Val Val Gly Lys Gln Leu Asn Glu
 1               5                  10                  15

Gln Pro Asp His Ser Pro Leu Val Gln Pro Gly Leu Ala Glu Leu Arg
            20                  25                  30

Arg Arg Ala Gln Glu Glu Gly Val Pro Glu Thr Pro Gln Pro Leu Thr
        35                  40                  45

Asp Ala Phe Leu Leu Arg Phe Leu Arg Ala Arg Asp Phe Asp Leu Asp
    50                  55                  60

Leu Ala Trp Arg Leu Met Lys Asn Tyr Tyr Lys Trp Arg Ala Glu Cys
65                  70                  75                  80

Pro Glu Leu Ser Ala Asp Leu His Pro Arg Ser Ile Leu Gly Leu Leu
                85                  90                  95

Lys Ala Gly Tyr His Gly Val Leu Arg Ser Arg Asp Pro Thr Gly Ser
            100                 105                 110

Arg Val Leu Ile Tyr Arg Ile Ser Tyr Trp Asp Pro Lys Val Phe Thr
        115                 120                 125

Ala Tyr Asp Val Phe Arg Val Ser Leu Ile Thr Ser Glu Leu Ile Val
    130                 135                 140

Gln Glu Val Glu Thr Gln Arg Asn Gly Val Lys Ala Ile Phe Asp Leu
145                 150                 155                 160

Glu Gly Trp Gln Ile Ser His Ala Phe Gln Ile Thr Pro Ser Val Ala
                165                 170                 175

Lys Lys Ile Ala Ala Val Val Thr Asp Ser Phe Pro Leu Lys Val Arg
            180                 185                 190

Gly Ile His Leu Ile Asn Glu Pro Val Ile Phe His Ala Val Phe Ser
        195                 200                 205

Met Ile Lys Pro Phe Leu Thr Glu Lys Ile Lys Gly Arg Ile His Leu
    210                 215                 220

His Gly Asn Asn Tyr Lys Ser Ser Leu Leu Gln His Phe Pro Asp Ile
225                 230                 235                 240

Leu Pro Leu Glu Tyr Gly Gly Asn Glu Ser Ser Met Glu Asp Ile Cys
                245                 250                 255

Gln Glu Trp Thr Asn Phe Ile Met Lys Ser Glu Asp Tyr Leu Ser Ser
            260                 265                 270

Ile Ser Glu Thr Ile Gln
        275
```

(2) INFORMATION FOR SEQ ID NO:24:

(i) SEQUENCE CHARACTERISTICS:
        (A) LENGTH: 4 amino acids
        (B) TYPE: amino acid
        (C) STRANDEDNESS: single

```
            (D) TOPOLOGY: linear (ii) MOLECULE TYPE: peptide (xi) SEQUENCE DESCRIPTION: SEQ ID NO:24:

Leu Leu His Pro
1

(2) INFORMATION FOR SEQ ID NO:25:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

Gly Ser Phe Leu Met Leu Phe Lys Ser Leu His Pro
1               5                   10
```